United States Patent
Ngo et al.

(10) Patent No.: US 8,118,042 B2
(45) Date of Patent: Feb. 21, 2012

(54) APPARATUS AND METHOD FOR CLEANING A LIQUID HANDLING PROBE

(75) Inventors: Dang M. Ngo, Fountain Valley, CA (US); Kinh N. Vo, Brea, CA (US); Paul R. Meyer, Shakopee, MN (US); Jon P. Lindquist, Coon Rapids, MN (US); Alan N. Johnson, Chaska, MN (US)

(73) Assignee: Beckman Coulter, Inc., Brea, CA (US)

( * ) Notice: Subject to any disclaimer, the term of this patent is extended or adjusted under 35 U.S.C. 154(b) by 336 days.

(21) Appl. No.: 12/395,590

(22) Filed: Feb. 27, 2009

(65) Prior Publication Data
US 2009/0217951 A1    Sep. 3, 2009

Related U.S. Application Data

(60) Provisional application No. 61/032,907, filed on Feb. 29, 2008.

(51) Int. Cl.
*B08B 3/04* (2006.01)

(52) U.S. Cl. .......... 134/95.2; 134/100.1; 134/102.2; 134/166 C; 134/169 C

(58) Field of Classification Search ........... 134/166 C, 134/169 C, 168 C, 95.2, 100.1, 102.2
See application file for complete search history.

(56) References Cited

U.S. PATENT DOCUMENTS

| | | | |
|---|---|---|---|
| 3,522,824 A * | 8/1970 | Allen | 141/90 |
| 3,577,279 A | 5/1971 | Lightner et al. | |
| 3,706,413 A * | 12/1972 | Blum | 494/11 |
| 4,098,305 A * | 7/1978 | Gates | 141/92 |
| 4,155,978 A * | 5/1979 | Naono et al. | 422/64 |
| 4,200,607 A * | 4/1980 | Suzuki | 422/64 |
| 4,318,884 A | 3/1982 | Suzuki | |
| 4,857,056 A * | 8/1989 | Talonn | 604/135 |
| 5,474,744 A | 12/1995 | Lerch | |
| 5,506,142 A * | 4/1996 | Mahaffey et al. | 436/49 |
| 5,730,938 A * | 3/1998 | Carbonari et al. | 422/64 |
| 5,750,881 A | 5/1998 | Dorenkott et al. | |
| 5,820,824 A | 10/1998 | Tanaka | |
| 5,869,774 A | 2/1999 | Backlund et al. | |
| 6,322,752 B1 * | 11/2001 | Siddiqui et al. | 422/510 |

(Continued)

FOREIGN PATENT DOCUMENTS
EP    0 785 434    7/1997
(Continued)

OTHER PUBLICATIONS
WIPO WO 96/08726 Mar. 1996.*
(Continued)

*Primary Examiner* — Frankie L Stinson
(74) *Attorney, Agent, or Firm* — Merchant & Gould PC

(57) ABSTRACT

The present invention concerns an improved apparatus for cleaning the interior of a liquid handling probe to reduce the amount time and the volume of wash fluid required to clean the probe and minimize carryover of material between different samples. In addition to the probe, the apparatus includes one or more wash fluid reservoirs, a compressed gas supply, one or more pumps, two or more valve-controlled probe lines and a controller for opening and closing the valves and actuating the pump(s) at desired time intervals. The invention further concerns a method of cleaning a liquid handling probe using the claimed apparatus and comprising sequential steps of pumping wash fluid and compressed gas through the probe.

10 Claims, 3 Drawing Sheets

U.S. PATENT DOCUMENTS

| | | |
|---|---|---|
| 6,709,870 B2 * | 3/2004 | Suzuki et al. .................. 436/49 |
| 2005/0003458 A1 | 1/2005 | Moore et al. |
| 2006/0045810 A1 | 3/2006 | Choikhet et al. |
| 2006/0258011 A1 | 11/2006 | Shvets et al. |

FOREIGN PATENT DOCUMENTS

| | | | |
|---|---|---|---|
| EP | 1 508 791 | | 2/2005 |
| JP | 63-177064 | * | 7/1988 |
| JP | 04-117277 | * | 4/1992 |
| JP | 10-115622 A | | 5/1998 |
| JP | 11-198994 | * | 7/1999 |
| WO | WO-01/28701 | | 4/2001 |
| WO | WO-2005/010488 | | 2/2005 |

OTHER PUBLICATIONS

International Search Report and Written Opinion for PCT/US2009/035571, mailed Jun. 25, 2009, 11 pages.

* cited by examiner

APPARATUS AND METHOD FOR CLEANING A LIQUID HANDLING PROBE

CROSS-REFERENCE TO RELATED APPLICATIONS

This application claims the benefit of U.S. Ser. No. 61/032,907, filed Feb. 29, 2008, which is fully incorporated herein by reference.

FIELD OF INVENTION

The present invention relates to the field of liquid handling systems and more particularly to an improved apparatus and methods for cleaning the interior of a liquid handling probe to reduce the amount time and the volume of wash fluid required to clean the probe and minimize carryover of material between different samples or reagents.

BACKGROUND OF THE INVENTION

Automated clinical chemistry analyzers are well known in the art and generally use an aspirating device such as a sampling tip, probe or needle to transfer predetermined volumes of liquid samples or reagents between different receptacles, such as sample containers, reagent containers and reaction cuvettes positioned at various locations on the analyzer. The aspirating device, commonly referred to as a sample or reagent probe, is usually an elongated, needle-like component having a hollow passage whereby liquid may be drawn into and dispensed from the sample or reagent probe using an appropriate pump. Such sample or reagent probes may be used to aspirate and deliver liquid samples or reagents between different receptacles, either with the same liquid sample or reagent probe or with multiple probes.

A common problem in such aspirating probes is the risk of liquid carryover, which usually occurs when a probe having residual traces of a previously dispensed sample or reagent is introduced into the volume of a different sample or reagent, thereby interfering with subsequent analyses.

To reduce carryover, the liquid handling probe is typically cleaned by washing between successive cycles of operation. Probe washing may be accomplished, for example, by lowering the liquid handling probe into a wash cell that contains an appropriate wash fluid solution. The wash fluid solution directly washes the exterior of the probe, whereas the interior of the probe may be cleaned by aspirating and discharging the wash fluid solution. Alternatively, the probe may be cleaned by flushing a wash fluid from a separate wash fluid reservoir through the probe. In this manner, the volume of carryover on the exterior surface and/or the interior surface of the probe may usually be reduced.

A common problem with probe washing, however, is observed when residual sample or reagent is absorbed on the surface of the probe despite washing. This residual material may mix with subsequent samples or reagents drawn into the liquid handling probe and interfere with chemical analyses. Furthermore, the presence of additional residual droplets of sample or reagent on the interior and/or exterior surface of the probe may introduce unwanted additional volume of liquid into a destination receptacle, which is particularly problematic when sample volumes themselves are relatively small.

Another common problem with probe washing is the amount of time and the volume of wash fluid required to adequately clean the probe. Depending on the nature of samples or reagents, numerous lengthy wash cycles may be required, and large volumes of wash fluid may have to be flushed through the probe to achieve a desired degree of reduction in residual carryover. This is particularly problematic with clinical samples such as human blood or serum, since disposing of a large volume of biohazardous waste can be expensive and logistically difficult.

One possible solution to these problems is described in U.S. Pat. No. 5,506,142 and in its European counterpart EP0571611. These patents disclose a probe wash system and method of using the system wherein a turbulent, segmented flow of gas and fluid created in the probe by the simultaneous introduction of pressurized air and water is used to blow a residual carryover material out of the probe prior to washing the probe with additional wash fluid. One significant problem with such a system is that it is known to generate bubbles, which can become trapped inside the probe and subsequently introduced into a test chamber, thereby negatively affecting the accuracy of subsequent measurements. Thus, there remains a need for better devices and methods that would address the aforementioned limitations of existing probe cleaning technologies.

In this regard, an improved apparatus and method for cleaning a liquid handling probe that minimize carryover of material between different samples or reagents are disclosed herein. The disclosed embodiments effectively decrease the amount time needed to achieve the desired low levels of carryover and/or reduce the volume of wash fluid required to achieve the desired low levels of carryover between different samples or reagents.

SUMMARY OF THE INVENTION

An apparatus and method of the present invention solve these problems. It was surprisingly discovered by the inventors that sequential introduction of a wash fluid and pressurized gas into the probe lines to create an alternating fluid/gas wash improved cleaning efficiency by reducing the amount of time and the volume of wash fluid required to achieve the desired low levels of carryover of material between different samples or reagents. Moreover, the sequential addition of discrete and alternating segments of fluid and gas through the probe effectively addressed the bubble problem characteristic of earlier designs.

In one aspect, an improved apparatus for cleaning the interior surface of a probe used for aspirating successive liquid samples or reagents from different containers is disclosed.

The apparatus includes a wash fluid reservoir coupled to a liquid handling probe through a first probe line. The apparatus further includes a pump, which is coupled to the first probe line at an intermediate point between the probe and the wash fluid reservoir, for withdrawing wash fluid out of the wash fluid reservoir and for pumping it through the first probe line to the probe. Also included is a first valve for controlling the flow of the wash fluid between the reservoir and the probe. This first valve has two selectable positions. A first selectable position allows the flow of the wash fluid from the wash fluid reservoir to the pump, and a second selectable position prevents the backflow of the wash fluid from the pump to the reservoir and allows the flow of the wash fluid from the pump to the probe. A compressed gas supply is coupled to the first probe line through a second probe line via a connector located at an intermediate point between the probe and the first valve. Also provided is a second valve coupled to the second probe line at an intermediate point between the connector and the compressed gas supply, for controlling the flow of gas to the probe. This second valve has an open position for allowing the flow of gas from the compressed gas supply to the probe and a closed position for preventing the flow of gas from the compressed gas supply to the probe. A controller is further provided for actuating the first and second valves and the pump at desired time intervals.

The wash fluid preferably comprises water, more preferably an aqueous buffer solution, most preferably a phosphate-buffered saline solution, phosphate buffer, borate buffer, citrate buffer, Tris buffer, MOPS buffer, PIPES buffer or HEPES buffer. The compressed gas preferably comprises an inert gas such as, for example, nitrogen or a noble gas; most preferably, the compressed gas comprises air.

The first and second valves may comprise solenoid valves. More preferably, the first valve comprises a shear valve, while the second valve comprises a solenoid valve. The pump may comprise a syringe pump or a peristaltic pump, preferably a syringe pump. The connector may comprise a 3-way or a 4-way connector, preferably a T-junction connector.

The controller for actuating the first and second valves and the pump preferably comprises appropriate electric circuitry for controlling the volumes of wash fluid being aspirated and pumped and the time intervals at which specific components of the cleaning apparatus are actuated. In one embodiment, the controller comprises one or more software modules and computer hardware including one or more microprocessors for interpreting software instructions from a user.

It is understood, however, that other types of wash fluid, compressed gas, valves, pumps, connectors and controllers may also be used successfully according to the invention.

In another aspect, a method is provided for cleaning a liquid handling probe after an aspiration-dispensation cycle. In this aspect, effective probe cleaning is accomplished through a sequence of carefully controlled steps.

In the first step, the first valve is placed in the first selectable position, and the pump is actuated to withdraw a first predetermined volume of said wash fluid from the wash fluid reservoir into the pump. In the second step, the first valve is placed in the second selectable position and a second predetermined volume of the wash fluid is pumped from the pump through the first probe line to the probe, while maintaining the second valve in the closed position. In the third step, the pumping of the wash fluid is stopped and the interior surface of the probe is permitted to soak in the wash fluid to release and/or dissolve any material to be removed. In the fourth step, the second valve is opened to drive compressed gas through the probe and expel the wash fluid and the material to be removed from the probe, after which the second valve is closed. If time permits, steps 2-4 can optionally be repeated one or more times. In the last step, the first valve is once again placed in the first selectable position, the pump is actuated to withdraw the first predetermined volume of the wash fluid from the wash fluid reservoir into the pump, the first valve is switched to the second selectable position, and all the wash fluid from the pump is pumped through the probe to purge substantially all gas from the probe, while the second valve remains in the closed position. It is well known in the art that any gas pockets remaining in the probe may adversely affect the accuracy of subsequent aspiration-dispensation cycles.

The material to be removed is preferably a residual carryover material. The second predetermined volume is preferably smaller than the first predetermined volume so that two or more wash cycles may be carried out following a single aspiration of the wash fluid from the reservoir. Steps 2-4 of the probe cleaning method above are preferably executed more than once, more preferably at least twice, most preferably at least three times.

Sometimes it may be desirable to employ more than one wash fluid. This may be the case where a primary wash fluid used to clean the probe is itself a potential source of harmful carryover. In this scenario, one or more additional wash fluids may be used to minimize cross-contamination. Thus, in another aspect, a probe cleaning apparatus is provided wherein more than one wash fluid is employed to clean the probe. In one embodiment, the apparatus comprises multiple wash fluid reservoirs coupled to a liquid handling probe through a first valve having three or more selectable positions. The first valve is further coupled to multiple pumps. The number of pumps is preferably equal to the number of wash fluid reservoirs, but it may also be greater or lower than the number of wash fluid reservoirs. In an alternative configuration, multiple wash fluid reservoirs may be coupled to a probe through separate valves having two or more selectable positions. As discussed above, these valves preferably comprise shear valves but may alternatively comprise solenoid valves or other types of valves as well.

In operation, a multiple wash fluid configuration is similar to the single wash fluid configuration described above, with the exception that the operation further comprises the steps of alternating between using different wash fluid reservoirs and between different pumps coupled to those reservoirs in order to provide sequential cleaning of the probe with different wash fluids. Pulses of compressed gas are employed between the steps of flushing the probe with different wash fluids in the same manner as they are used in the single wash fluid configuration. The final flushing step preferably employs a common wash fluid such as, for example, water or a phosphate buffer, which does not usually present a significant carryover problem.

DETAILED DESCRIPTION OF THE INVENTION

The present inventions may be understood more readily by reference to the following detailed description of the preferred embodiments and the Examples included herein. All patents, patent applications, published applications and publications, websites and other published materials referred to throughout the entire disclosure herein are incorporated by reference in their entirety.

Unless otherwise noted, the terms used herein are to be understood according to conventional usage by those of ordinary skill in the relevant art. In the event that there is a plurality of definitions for terms herein, those in this section prevail. It is also to be understood that the terminology used herein is for the purpose of describing specific embodiments only and is not intended to be limiting.

As used herein, the singular form "a", "an" and "the" includes plural references unless indicated otherwise.

As used herein, the terms "coupled" and "connected" refer to either a direct physical contact between two mechanical components or an indirect connection through one or more passive or active intermediate members. For example, a passive intermediate member may comprise a probe line allowing fluid or gas to flow from one component to the other, whereas an active intermediate member may comprise a valve and/or a pump facilitating or preventing such flow. Such connection may be achieved with the two components and any additional intermediate members being integrally formed as a single unitary body with one another or with the two components and any additional intermediate members being attached to one another. Such connection may be permanent or alternatively may be removable or releasable in nature.

Figure 1:
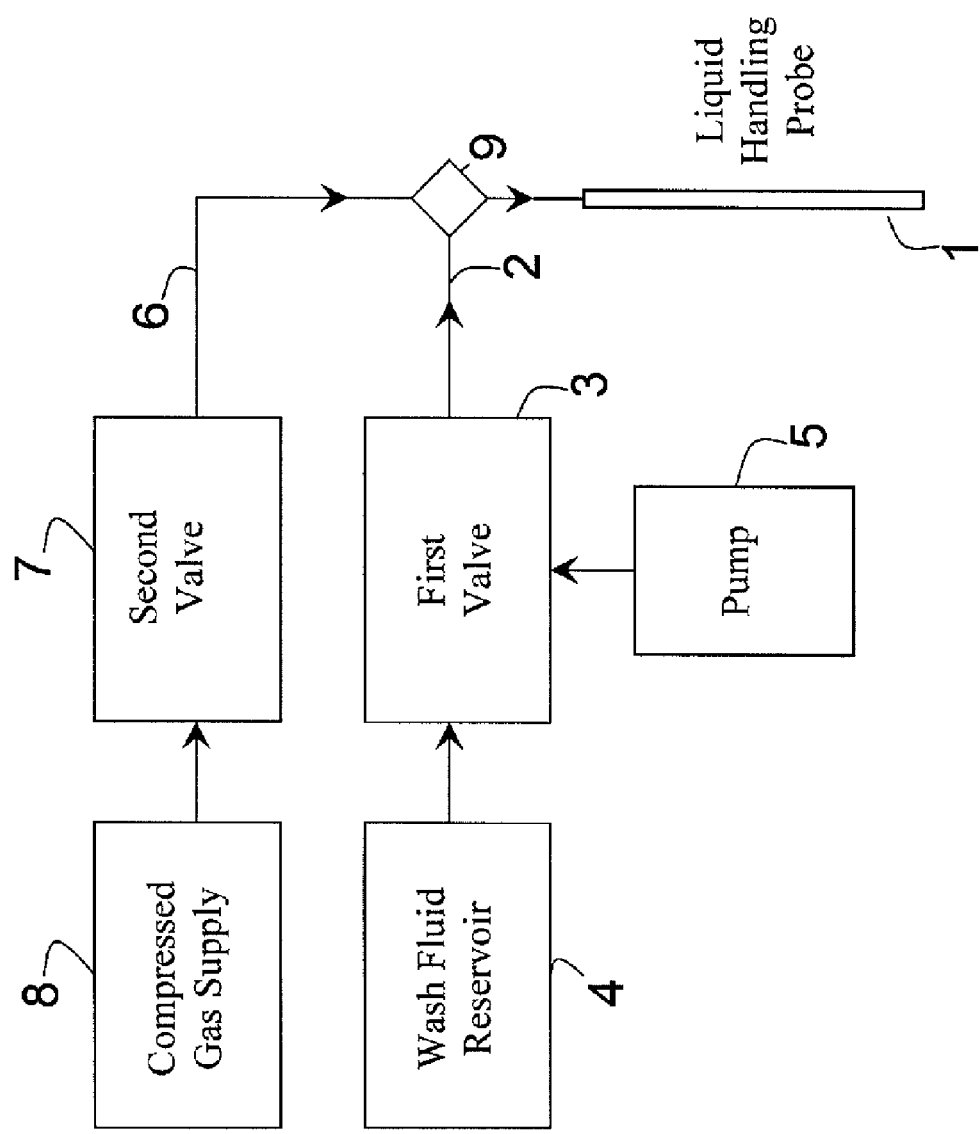
FIG. 1 is a schematic diagram illustrating a probe cleaning apparatus embodiment wherein a single wash fluid is employed.

Referring to FIG. 1, the first embodiment of a probe cleaning apparatus includes a wash fluid reservoir 4 coupled to an upper end of a liquid handling probe 1 through a first probe line 2 and a first valve 3, which valve is coupled to the first probe line 2 at an intermediate point between the liquid handling probe 1 and the wash fluid reservoir 4. In a preferred embodiment, the wash fluid comprises water or an aqueous buffer solution such as, for example, a phosphate-buffered saline solution, phosphate buffer, borate buffer, citrate buffer, Tris buffer, MOPS buffer, PIPES buffer or HEPES buffer. The pH of the buffer solution is preferably in the range between about 4.0 and about 9.0, more preferably between about 6.0 and about 8.0, and most preferably between about 7.0 and about 7.5. It is understood, however, that other appropriate wash fluids may also be used according to the invention.

The first valve 3 is further coupled to a pump 5, which is used to withdraw wash fluid from the wash fluid reservoir 4 and to pump the fluid through the first probe line 2 to the liquid handling probe 1. The first valve 3 has two selectable positions. In a first position, it allows the flow of the wash fluid from the wash fluid reservoir 4 to the pump 5. In a second position, it allows the flow of the wash fluid from the pump 5 through the first probe line 2 to the liquid handling probe 1, while preventing the backflow of the wash fluid from the pump 5 to the wash fluid reservoir 4. In a preferred embodiment, the first valve 3 comprises a shear valve or a solenoid valve, and the pump 5 comprises a syringe pump such as, for example, Hamilton PSD/2, PSD/3, PSD/4 or PSD/8, or a peristaltic pump. In the most preferred embodiment, the pump 5 comprises the Hamilton PSD/4 syringe pump, and the first valve 3 comprises a shear valve. It is understood that other types of valves and pumps may also be used according to the invention.

The apparatus further comprises a compressed gas supply 8 coupled to the first probe line 2 through a second probe line 6 and a connector 9. A second valve 7 is coupled to the second probe line 6 at an intermediate point between the connector 9 and the compressed gas supply 8. In some embodiments, the compressed gas may comprise air or an inert gas such as, for example, nitrogen or a noble gas; preferably the compressed gas comprises air. In some embodiments, the connector may comprise a 3-way or a 4-way connector, preferably a T-junction connector. However, it is understood that other types of connectors may also be used according to the invention.

The second valve 7 has an open position and a closed position. In the open position, it allows the flow of gas from the compressed gas supply 8 to the liquid handling probe 1. In the closed position, it prevents the flow of gas from the compressed gas supply 8 to the liquid handling probe 1. In a preferred embodiment, the second valve 7 comprises a solenoid valve, but it is understood that other types of valves may also be used according to the invention.

Not shown in FIG. 1, but also provided is a controller for actuating the first and second valves 3 and 7 and the pump 5. In a preferred embodiment, the controller comprises appropriate electric circuitry and one or more software modules for controlling the volumes of wash fluid aspirated and pumped and the time intervals at which specific components of the cleaning apparatus are actuated. In a preferred embodiment, the electric circuitry comprises computer hardware including one or more microprocessors for interpreting software instructions from a user.

In operation, the first valve 3 is first placed in the first selectable position so that the wash fluid can be aspirated from the wash fluid reservoir 4. The pump 5 is then actuated to withdraw a first predetermined volume of wash fluid from the wash fluid reservoir 4. Next, the first valve 3 is placed in the second selectable position so that the wash fluid can be pumped to the liquid handling probe 1, and the pump 5 is actuated again to pump a second predetermined volume of wash fluid through the first probe line 2 to the liquid handling probe 1. The second valve 7 remains in the closed position during all these steps to prevent introduction of gas into the wash fluid. When the pumping of the wash fluid is stopped, the interior surface of the liquid handling probe 1 is permitted to soak in the wash fluid for a predetermined amount of time to release and/or dissolve a material to be removed from the interior surface. The soaking step typically takes from about 0.1 to about 10 seconds, more preferably from about 0.3 to about 5 seconds, and most preferably from about 0.5 to about 2 seconds.

The second valve 7 is then opened to drive compressed gas through the liquid handling probe 1 and expel the wash fluid and the material to be removed from the probe, after which the second valve 7 is closed.

The steps of filling the liquid handling probe 1 with wash fluid, allowing the probe to soak in the wash fluid, and expelling the wash fluid from the probe using compressed gas can optionally be repeated one or more times, depending on the nature of samples or reagents being transferred.

In the final step of operation, the first valve 3 is again placed in the first selectable position, the pump 5 is actuated to withdraw the first predetermined volume of the wash fluid from the wash fluid reservoir 4, the first valve 3 is switched to the second selectable position, and all the wash fluid from the pump 5 is pumped through the first probe line 2 to purge substantially all gas from the liquid handling probe 1, while the second valve 7 remains closed.

It is well known in the art that any gas pockets remaining in the probe may adversely affect the accuracy of subsequent aspiration-dispensation cycles. As used herein, the term "substantially all gas" preferably means at least 50%, more preferably at least 60%, more preferably at least 70%, more preferably at least 80%, more preferably at least 90%, more preferably at least 95%, and most preferably at least 99% of the volume inside the probe.

The material to be removed preferably comprises a residual carryover material, however, it is understood that any undesired material may be removed by the method disclosed and claimed herein. The second predetermined volume typically falls into the range between about 0.1 and about 10 ml, more preferably between about 0.3 and about 5 ml, and most preferably between about 0.5 and about 2 ml. The second predetermined volume is preferably smaller than the first predetermined volume so that two or more wash cycles may be carried out following a single aspiration of the wash fluid from the reservoir.

In another preferred embodiment, the steps of filling the liquid handling probe 1 with the wash fluid, allowing the probe to soak in the wash fluid, and expelling the wash fluid from the probe using compressed gas are executed more than once, more preferably at least twice, and most preferably at least three times.

Figure 2:
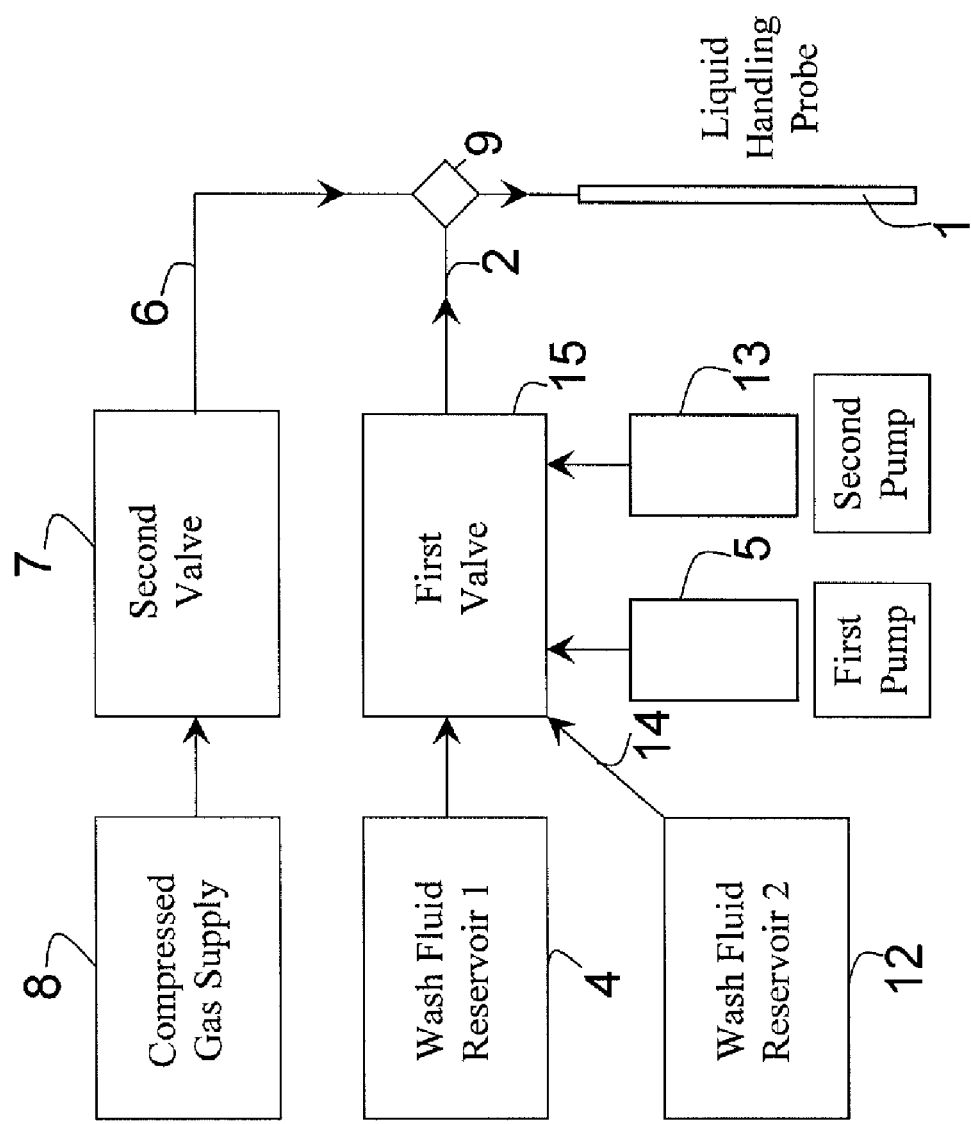
FIG. 2 illustrates a probe cleaning apparatus according to an alternative embodiment wherein multiple wash fluids are employed.

Referring now to FIG. 2, an alternative embodiment of a probe cleaning apparatus further comprises a second wash fluid reservoir 12 which contains a different wash fluid than the wash fluid in the first wash fluid reservoir 4. In addition to the first fluid reservoir 4, the second wash fluid reservoir 12 is coupled to a first valve 15 through a third probe line 14. A first pump 5 and a second pump 13 are coupled to the first valve 15. The first pump 5 is used to aspirate the wash fluid from the first wash fluid reservoir 4, whereas the second pump 13 is used to aspirate the wash fluid from the second wash fluid reservoir 12. In this embodiment, the first valve 15 has three selectable positions. In a first position, it allows the flow of the wash fluid from the first wash fluid reservoir 4 to the first pump 5. In a second position, it allows the flow of the wash fluid from the second wash fluid reservoir 12 to the second pump 13. In a third position, it allows the flow of the wash fluid from the first pump 5 or the second pump 13 through the first probe line 2 to the liquid handling probe 1, while preventing the backflow of the wash fluids from the first pump 5 and the second pump 13 to the first wash fluid reservoir 4 and the second wash fluid reservoir 12, respectively. The first valve 15 preferably comprises a shear valve or a solenoid valve, more preferably a shear valve. In operation, one or more liquid-gas wash cycles as described above using the wash fluid from the first wash fluid reservoir 4 may be followed by one or more liquid-gas wash cycles using the wash fluid from the second wash fluid reservoir 12. The net effect is minimization of the presence of the first wash fluid in the liquid handling probe 1 where such presence may have an undesirable effect on subsequent sample transfers.

Figure 3:
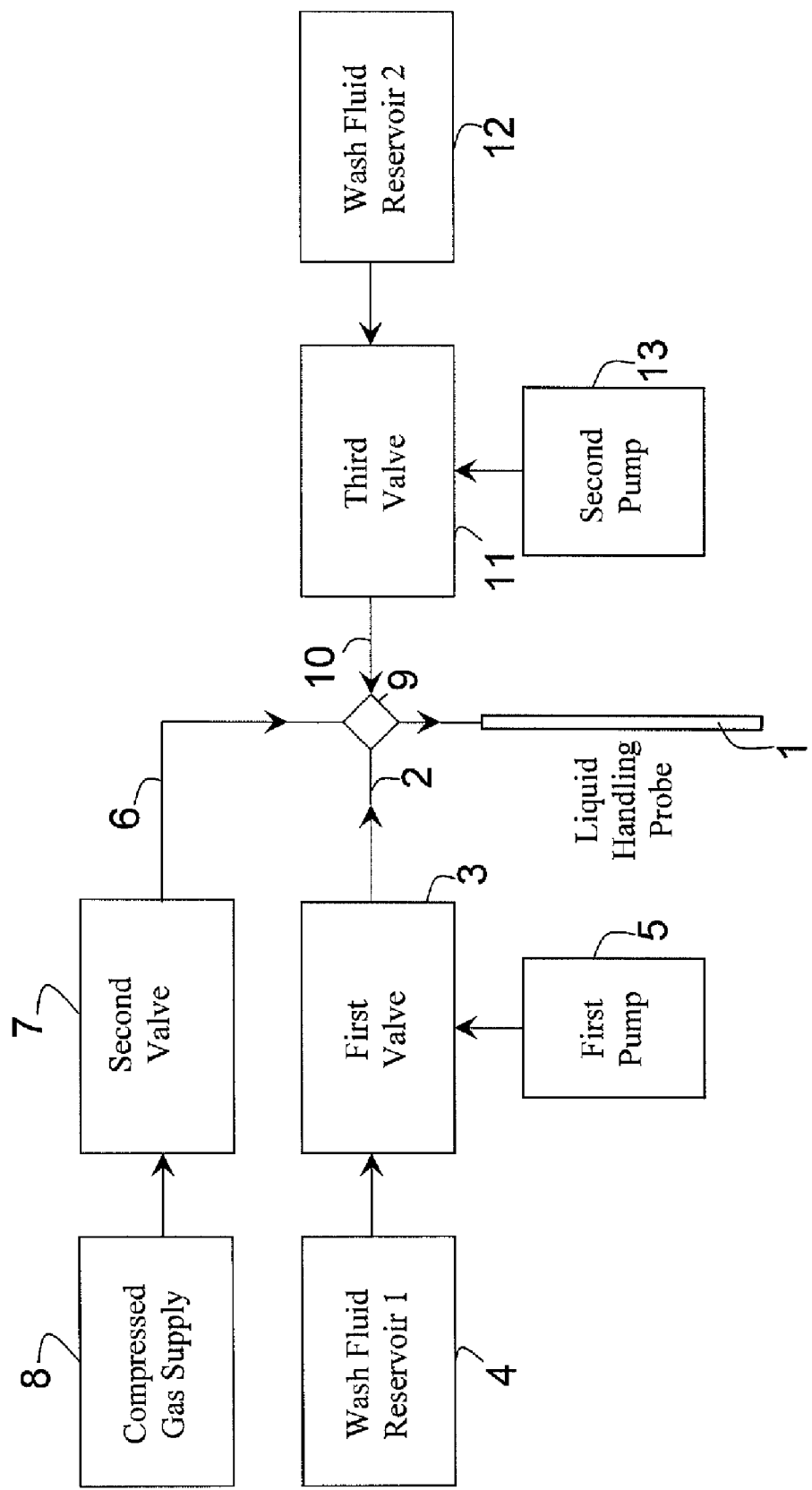
FIG. 3 illustrates a probe cleaning apparatus according to another alternative embodiment wherein multiple wash fluids are employed.

Referring now to FIG. 3, another alternative embodiment of a probe cleaning apparatus also comprises a second wash fluid reservoir 12 which contains a different wash fluid than the wash fluid in the first wash fluid reservoir 4. However, in this configuration the second wash fluid reservoir 12 is coupled to a third valve 11. The third valve 11 is coupled to a second pump 13 and also coupled to the connector 9 through a third probe line 10. The third valve 11 may have two selectable positions like the first valve 3 in FIG. 1 or, alternatively, it may have three selectable positions like the first valve 15 in FIG. 2. In operation, this alternative configuration is similar to the one shown in FIG. 2. One or more liquid-gas wash cycles as described above using the wash fluid from the first wash fluid reservoir 4 may be followed by one or more liquid-gas wash cycles using the wash fluid from the second wash fluid reservoir 12. As explained above, the aim here is to minimize the presence of the first wash fluid in the liquid handling probe 1 where such presence may have an undesirable effect on subsequent sample transfers.

It is understood, however, that the dual wash fluid configurations shown in FIGS. 2 and 3 are for illustration purposes only and are not intended to limit the scope of the inventions disclosed herein. A person skilled in the art would easily recognize that additional alternative configurations comprising more than two sources of wash fluids are also contemplated within the present invention. Using commercially available valves, pumps and connectors, one can assemble a cleaning apparatus according to the invention, comprising up to eight different wash fluid reservoirs. As explained elsewhere in this specification, the number of pumps is preferably equal to the number of different wash fluid reservoirs used, but it may also be greater or lower than the number of the wash fluid reservoirs.

The present inventions will be further described with reference to the following examples; however, it is to be understood that the inventions are not limited to such examples. The following examples are not intended to limit the scope of any claims, but are rather intended to be exemplary of certain embodiments. Any variations in the exemplified methods that occur to the skilled artisan are intended to fall within the scope one or more of the present invention.

EXAMPLES

Example 1

Sample Air-Assisted Wash Protocol

Table 1 summarizes a sample air-assisted wash protocol contemplated within the present invention. In this particular embodiment, an aqueous wash buffer (Beckman #A16793) and compressed air are employed; the first valve is a shear valve; the second valve is a solenoid valve (SMC #LVM13R-5A-2); and the pump is a syringe pump (Hamilton #PSD4). Before the probe aspirates and dispenses a sample, the syringe pump is turned on to withdraw 2.50 ml of wash buffer from the wash buffer reservoir. When the probe is done dispensing, it is already filled with wash buffer and residual carryover material.

At time 0.0 sec, a 0.9 sec pulse of compressed air is used to expel the wash buffer and the residual carryover material, after which the syringe pump dispenses 1.25 ml (50% of its capacity) over 1.7 sec into the probe. The interior surface of the probe is then soaked in the wash buffer for 1.3 sec, and a 1.0 sec pulse of compressed air expels the wash buffer from the probe again. At time 4.9 sec, the syringe pump dispenses another 1.25 ml of wash buffer into the probe, and the interior surface of the probe is soaked in the wash buffer for 0.6 sec. Finally, the third 1.0 sec pulse of compressed air expels the wash buffer from the probe. Following the last pulse of compressed air, the syringe pump aspirates 2.50 ml of wash buffer from the reservoir and dispenses the entire 2.50 ml into the probe in an effort to eliminate substantially all air pockets from the probe.

TABLE 1

Sample air-assisted probe wash protocol

| Start (sec) | Stop (sec) | Duration | Action |
| --- | --- | --- | --- |
| Before start of wash | | | Shear valve is switched to wash buffer reservoir and syringe pump is actuated to aspirate 2.50 ml of wash buffer |
| 0.0 | 0.9 | 0.9 | Solenoid valve is turned on to drive air through probe |
| 0.9 | 2.6 | 1.7 | Shear valve is switched to probe line and syringe pump is actuated to dispense 1.25 ml of wash buffer into probe |
| 2.6 | 3.9 | 1.3 | Interior surface of probe is soaked in wash buffer |
| 3.9 | 4.9 | 1.0 | Solenoid valve is turned on to drive air through probe |
| 4.9 | 6.6 | 1.7 | Syringe pump is actuated to dispense 1.25 ml of wash buffer into probe |
| 6.6 | 7.2 | 0.6 | Interior surface of probe is soaked in wash buffer |
| 7.2 | 8.2 | 1.0 | Solenoid valve is turned on to drive air through probe |
| After end of wash | | | Shear valve is switched to wash buffer reservoir and syringe pump is actuated to aspirate 2.50 ml of wash buffer; then shear valve is switched back to probe line and syringe pump is actuated to dispense 2.50 ml of wash fluid into probe to eliminate air pockets from the probe |

Example 2

Performance of Air-Assisted Wash in Selected Bioassays

Table 2 demonstrates the wash times (in seconds), the volumes of wash buffer (in milliliters), and the resulting carryovers (in part per million) produced by the air-assisted wash method described in Example 1 in four different diagnostic assays. BhCG refers to total beta-human chorionic gonadotropin test (Access Total βhCG, Beckman Coulter #33500); AFP refers to alpha-fetoprotein test (AFP 300 Test Kit, Beckman Coulter #33211); PSA refers to total prostate specific antigen test (Access Hybritech PSA, Beckman Coulter #37200); and free PSA refers to free prostate specific antigen test (Access Hybritech Free PSA, Beckman Coulter #37210)

TABLE 2

Performance of air-assisted probe wash in selected bioassays

| | Air-Assisted Wash | | |
|---|---|---|---|
| Assay | Time (sec) | Volume (ml) | Carryover (ppm) |
| BhCG | 8.2 | 5.0 | 1.79 |
| AFP | 8.2 | 5.0 | 0.21 |
| PSA | 8.2 | 5.0 | 3.36 |
| Free PSA | 8.2 | 5.0 | 2.97 |

Example 3

Comparison of Air-Assisted Wash with Alternative Wash Protocols

Table 3 shows a comparison of the wash times, the volumes of wash buffer, and the resulting carryovers produced by the air-assisted wash method described in Example 1 and two alternative wash protocols in the BhCG diagnostic assay (Access Total βhCG, Beckman Coulter #33500).

In the Active Wash protocol, a probe filled with wash fluid was lowered into a wash cell that was also filled with wash fluid. The wash cell was then engaged in a rocking motion for a predetermined period of time, thereby causing its side wall to contact the probe and thus effect dissociation of residual carryover material from the interior and exterior surfaces of the probe. Once the rocking motion was stopped, a pump was employed to expel the wash liquid from inside the probe. In the Superwash protocol, the same basic steps were maintained, but additional 12 seconds were added to the wash to further reduce carryover.

TABLE 3

Comparison of air-assisted probe wash with alternative wash protocols

| | Air-Assisted Wash | | | Active Wash | | | Superwash | | |
|---|---|---|---|---|---|---|---|---|---|
| Assay | Time (sec) | Volume (ml) | Carryover (ppm) | Time (sec) | Volume (ml) | Carryover (ppm) | Time (sec) | Volume (ml) | Carryover (ppm) |
| BhCG | 8.2 | 5.0 | 1.79 | 18.8 | 4.0 | 24.65 | 30.8 | 6.0 | 2.10 |

As Table 3 shows, the Air-Assisted Wash protocol took the least amount of time to complete and resulted in the lowest carryover. Although the carryover resulting from the Superwash protocol was comparable to that yielded by the Air-Assisted Wash protocol, Superwash took almost four times as long to complete as Air-Assisted Wash (30.8 v. 8.2 sec).

The invention claimed is:

1. An apparatus for cleaning a liquid handling probe, the apparatus comprising:
   a liquid handling probe having an interior surface, an exterior surface, an upper end and a lower end;
   a first probe line coupled to said upper end of said probe;
   a wash fluid reservoir coupled to said first probe line;
   a pump coupled to said first probe line at an intermediate point between said probe and said reservoir for withdrawing wash fluid from said wash fluid reservoir and for pumping it to said probe;
   a first valve coupled to said pump, having a first selectable position for allowing the flow of said wash fluid from said reservoir to said pump and having a second selectable position for preventing the backflow of said wash fluid from said pump to said reservoir and for allowing the flow of said wash fluid from said pump to said probe;
   a second probe line coupled to said first probe line at a connector at an intermediate point between said probe and said first valve;
   a compressed gas supply coupled to said second probe line;
   a second valve coupled to said second probe line at an intermediate point between said connector and said compressed gas supply, having an open position for allowing the flow of gas from said compressed gas supply to said probe and having a closed position for preventing the flow of gas from said compressed gas supply to said probe;
   a second wash fluid reservoir containing a second wash fluid connected to said first valve by a third probe line and a second pump connected to said first valve, said first valve having a third selectable position allowing the flow of wash fluid from the second wash fluid reservoir to the second pump and a fourth selectable position for preventing backflow of said second wash fluid from the second pump to the second reservoir and allowing the flow of the second wash fluid from the second pump to said probe; and
   a controller for actuating said first and second valves and said pump at desired time intervals.

2. The apparatus of claim 1, wherein said first valve comprises a shear valve.

3. The apparatus of claim 1, wherein said first valve comprises a solenoid valve.

4. The apparatus of claim 1, wherein said second valve comprises a solenoid valve.

5. The apparatus of claim 1, wherein said pump comprises a syringe pump.

6. The apparatus of claim 1, wherein said pump comprises a peristaltic pump.

7. The apparatus of claim 1, wherein said connector comprises a three-way or a four-way connector.

8. The apparatus of claim 1, in which the pump retains sufficient wash fluid from a single aspiration from the reservoir to repeatedly dispense wash fluid to the probe.

9. The apparatus of claim 1, wherein the second wash fluid is a different from the wash fluid in the reservoir of claim 1.

10. The apparatus of claim 9, wherein the second wash fluid is water.

* * * * *